United States Patent [19]
Oediger

[11] 3,998,857
[45] Dec. 21, 1976

[54] PROCESS FOR PREPARING ANTHRAQUINONE

[75] Inventor: Hermann Oediger, Cologne, Germany

[73] Assignee: Bayer Aktiengesellschaft, Leverkusen, Germany

[22] Filed: July 9, 1975

[21] Appl. No.: 594,485

[30] Foreign Application Priority Data
Aug. 2, 1974 Germany .......................... 2437220

[52] U.S. Cl. .............................................. 260/369
[51] Int. Cl.² .......................................... C09B 1/00
[58] Field of Search .................................... 260/369

[56] References Cited
UNITED STATES PATENTS

| | | | |
|---|---|---|---|
| 2,072,867 | 3/1937 | Carothers | 260/369 X |
| 2,938,913 | 5/1960 | Weyker et al. | 260/369 |
| 3,870,730 | 3/1975 | Scharfe et al. | 260/369 |

*Primary Examiner*—Paul F. Shaver
*Attorney, Agent, or Firm*—Burgess, Dinklage & Sprung

[57] ABSTRACT

Anthraquinones are prepared by reacting a 1,4-naphthoquinone with trans-1-acetoxybutadiene in a polar solvent at a temperature of from 30° to 60° C, optionally in the presence of acetic acid. 1-acetoxy-1,4,4a,9a-tetrahydroanthraquinone is produced which is then treated with oxygen at temperatures of 100° to 130° C without isolation, optionally after adding a salt of acetic acid or a compound which forms an acetic acid salt under the reaction conditions.

10 Claims, No Drawings

PROCESS FOR PREPARING ANTHRAQUINONE

The present invention relates to a process for the preparation of anthraquinone by reaction of 1,4-naphthoquinone with trans-1-acetoxybutadiene. Anthraquinone is required as a starting product for the preparation of the anthraquinone dyestuffs.

It is known from German Pat. No. 739,438, to obtain anthraquinone by reaction of 1,4-naphthoquinone with excess 1-acetoxybutadiene at the reflux temperature. However, the yield is only 57% of theory. Furthermore it is known, from Liebig's Ann. Chem. volume 568 (1950), page 28, to warm 1,4-naphthoquinone with excess 1-acetoxybutadiene in acetic acid, separate off the resulting anthraquinone (19% of theory), isolate from the reaction solution the addition product first formed from 1,4-naphthoquinone and 1-acetoxybutadiene, namely 1-acetoxy-1,4,4a,9a-tetrahydroanthraquinone, and convert this into anthraquinone by means of methanolic potassium hydroxide solution in the presence of air. While this process gives a total yield of anthraquinone of about 80% of theory, it is unsuitable for large scale industrial use.

This is also true of the process described in Journal of Pharmaceutical Sciences, volume 53 (1964), page 624, in which 1,4-naphthoquinone is first condensed with 1-acetoxybutadiene in benzene and the condensation product first formed is then isolated and converted into anthraquinone by means of methanolic ammonia solution or by means of sodium methylate in methanol.

SUMMARY

In accordance with this invention anthraquinones are obtained by reaction of 1,4-naphthoquinones with trans-1-acetoxybutadiene in a polar solvent at a temperature of from 30° to 60° C, if appropriate in the presence of acetic acid to give 1-acetoxy-1,4,4a,9a-tetrahydroanthraquinone and treating the reaction solution thus obtained with oxygen at a temperature of from 100° to 130° C, without isolation of the 1-acetoxy-1,4,4a,9a-tetrahydroanthraquinone, if appropriate after addition of a salt of acetic acid or of a compound which forms an acetic acid salt under the reaction conditions.

The process according to the invention can give pure anthraquinones in yields which are far above the yields of the known processes. The process according to the invention further has the advantage that the anthraquinones are prepard without isolating the condensation product of 1,4-naphthoquinone and trans-1-acetoxybutadiene. Although the present invention is suitable primarily for the preparation of anthraquinone itself, substituted anthraquinones can be prepared by the method of the invention by using appropriately-substituted starting materials. Thus, any 1,4-naphthoquinone substituted in the aromatic nucleus may be used as starting material, provided that the substituent group (or groups) does not interfere with the reaction.

DESCRIPTION

The 1,4-naphthoquinone can be employed in the process either in the pure form or in the form in which it arises when manufactured industrially by catalytic oxidation of naphthalene. 1,4-Naphthoquinone industrially manufactured in this way in general contains varying amounts of phthalic anhydride in addition to naphthalene. Purification for use within the scope of the process according to the invention is not necessary. Phthalic anhydride remains in the reaction solution after separating off the anthraquinone; it can then be obtained from the solution by simple evaporation of the solvent and can, if appropriate, be employed for other processes.

Trans-1-acetoxybutadiene is known; for example, its preparation from crotonaldehyde and acetic acid isopropenyl ester is described in J. Org. Chem. volume 21 (1956), page 330. Trans-1-acetoxybutadiene can furthermore be prepared from crotonaldehyde, acetic anhydride and sodium acetate (J. Pr. Chem. (2), volume 157 (1941), page 198).

As solvents it is possible to use those polar solvents in which 1,4-naphthoquinone and 1-acetoxy-1,4,4a,9a-tetrahydroanthraquinone are soluble at room temperature. Preferred polar solvents for this purpose are those which have a boiling point above the decomposition temperature of 1-acetoxy-1,4,4a,9a-tetrahydroanthraquinone. However, this is not critical. If the boiling point of the polar solvent is below this decomposition temperature, the reaction is completed under pressure.

Examples of polar solvents which can be used are N,N-dialkylformamides with straight-chain or branched alkyl radicals with up to 5 C atoms, $C_1$- to $C_3$-alkyl radicals being preferred. As examples of individual compounds there may be mentioned N,N-dimethylformamide, N,N-diethylformamide and N,N-di-n-propylformamide.

Further polar solvents which can be used are N,N-dialkylacetamides having straight-chain or branched alkyl groups with up to 5 C atoms each, $C_1$- to $C_3$-alkyl radicals being preferred. As examples of individual compounds there may be mentioned N,N-dimethylacetamide, N,N-diethylacetamide and N,N-di-n-propylacetamide.

Further possibilities are nitriles of aliphatic carboxylic acids with up to 5 C atoms. As examples of individual compounds there may be mentioned acetonitrile, propionitrile and isobutyronitrile. The use of acetonitrile is preferred.

Further possibilities are optionally $C_1$-$C_4$-alkyl-substituted heterocyclic nitrogen compounds. N-Methylpyrrolidone may be mentioned as an example.

Possible salts of acetic acid which are optionally employed within the scope of the process according to the invention are salts of the alkali metals and alkaline earth metals as well as salts of heavy metals of subgroup I of the Periodic Table, such as copper and silver. Examples which may be mentioned are sodium acetate, potassium acetate, barium acetate and calcium acetate. Sodium acetate and potassium acetate are particularly preferred. Copper acetate may be mentioned as an example of the heavy metal salts of acetic acid.

Possible compounds which form salts of acetic acid under the reaction conditions are preferentially the carbonates, bicarbonates and hydroxides of the metals, those of the alkali metals and alkaline earth metals being employed preferentially. Examples which may be mentioned are sodium bicarbonate, sodium carbonate, potassium bicarbonate, potassium carbonate, sodium hydroxide, potassium hydroxide, calcium hydroxide and barium hydroxide.

The process according to the invention is optionally carried out in the presence of acetic acid, which is then generally employed in amounts of 0.1 to 2 mols per mol of 1,4-naphthoquinone.

The reaction, in the first stage, is in general carried out at temperatures of 30° to 60° C, preferably at 40° to 50° C. Preferably, this reaction is carried out with substantial exclusion of oxygen, in an inert gas atmosphere. Examples of possible inert gases are nitrogen and argon. The reaction time depends on the reaction temperature and is about 5 – 6 hours at 50° C. The treatment of the reaction solution, in the second stage, with oxygen is in general carried out at temperatures of 100° – 130° C, preferably at 110° – 120° C. The reaction time here again depends on the reaction temperature and is 2 – 3 hours at 120° C.

The treatment with oxygen can either be carried out by passing pure oxygen into the reaction solution or by using gas mixtures which contain oxygen. The use of air is preferred.

Suitably, at least 1 mol of trans-1-acetoxybutadiene is employed per mol of 1,4-naphthoquinone. In general, amounts of 1.1 – 1.2 mols of trans-1-acetoxybutadiene per mol of 1,4-naphthoquinone will be employed. A larger excess of trans-1-acetoxybutadiene is not disadvantageous, but is inappropriate for economic reasons. 0.1 – 2 mols of acetic acid are employed per mol of 1,4-naphthoquinone. If a salt of acetic acid or of a compound which forms an acetate under the reaction conditions is added, it is in general in amounts of 0.03–0.06 mol, preferably 0.04 – 0.05 mol, per mol of 1,4-naphthoquinone. The anthraquinone then precipitates from the reaction solution and can thus be separated off in a simple manner. The solvent and acetic acid can be recovered by a simple distillation and be returned to the process according to the invention, a method of working which improves the economics of the process.

The invention is illustrated in the following examples in which 96 % pure naphthoquinone is used, unless stated otherwise. The following reaction scheme illustrates the process of the present invention.

and 13.5 parts by weight of 1-acetoxybutadiene in 50 parts by volume of dimethylacetamide and 1 part by volume of acetic acid are stirred under nitrogen for 5 hours at 50° – 55° C. 0.4 part by weight of potassium acetate is then added, air is passed in and the batch is stirred for 3 hours at 120° C. After cooling, the anthraquinone which has precipitated is filtered off and washed with dimethylacetamide. 18.6 parts by weight (93% of theory) of anthraquinone of melting point 284° C are obtained.

EXAMPLE 3 TO 13

In each example, the procedure followed is as indicated in Example 1 except that the sodium acetate is replaced by the catalysts indicated in the table which follows.

Table

Anthraquinone from 1-acetoxybutadiene and 1,4-naphthoquinone

| Example No. | Catalyst (amount in parts by weight) | Anthraquinone (yield in % of theory) |
|---|---|---|
| 3 | 0.5 potassium acetate | 92 |
| 4 | 0.8 copper acetate | 87 |
| 5 | 0.3 sodium carbonate | 92 |
| 6 | 0.6 sodium bicarbonate | 91 |
| 7 | 0.3 potassium carbonate | 93 |
| 8 | 0.4 potassium bicarbonate | 90 |
| 9 | 0.7 calcium acetate | 89 |
| 10 | 0.9 barium acetate | 86 |
| 11 | 0.2 sodium hydroxide | 93 |
| 12 | 0.3 potassium hydroxide | 92 |
| 13 | 0.4 calcium hydroxide | 87 |

EXAMPLE 14

15.8 parts by weight of naphthoquinone and 13.0 parts by weight of 1-acetoxybutadiene in 40 parts by volume of dimethylformamide and 10 parts by volume of acetic acid are stirred for 6 hours under nitrogen at

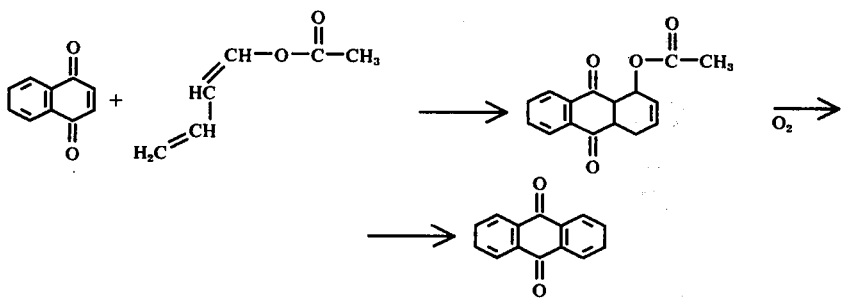

EXAMPLE 1

15.8 parts by weight naphthoquinone and 13.5 parts by weight of 1-acetoxybutadiene in 50 parts by volume of dimethylformamide and 1 part by volume of acetic acid are stirred for 6 hours under nitrogen at 45° – 50° C. 0.4 part by weight of sodium acetate is then added, oxygen is passed in and the batch is stirred for 2 hours at 120° C. After cooling, the anthraquinone which has precipitated is filtered off and washed with dimethylformamide. 18.2 parts by weight (91% of theory) of anthraquinone of melting point 284° C are obtained.

EXAMPLE 2

20.8 parts by weight of technical naphthoquinone, which contains 5 parts by weight of phthalic anhydride, 45° – 50° C. Air is then passed in and the batch is stirred for 2 hours at 125° C. After cooling, the anthraquinone which has precipitated is filtered off and washed with dimethylformamide. 18.0 g (90% of theory) of anthraquinone of melting point 284° C are obtained.

EXAMPLE 15

20.8 parts by weight of technical naphthoquinone, which contain 5 parts by weight of phthalic anhydride, and 13.5 parts by weight of 1-acetoxybutadiene are reacted, as described in Example 4, in 55 parts by volume of the solvent mixture which arises according to Example 4 and has been freed from anthraquinone. 17.8 g (89% of theory) of anthraquinone of melting point 284° C are obtained.

What is claimed is:

1. Process for preparing anthraquinones which comprises reacting a 1,4-naphthoquinone with trans-1-acetoxybutadiene in a polar solvent at a temperature of from 30° to 60° C, optionally in the presence of acetic acid, to give 1-acetoxy-1,4,4a,9a-tetrahydroanthraquinone and treating the reaction solution obtained with oxygen at a temperature of from 100° to 130° C without isolation of said 1-acetoxy-1,4,4a,9a-tetrahydroanthraquinone, after addition of a salt of acetic acid or of a compound which forms an acetic acid salt under the reaction conditions, about 0.03 to 0.06 mol of the acetic acid salt or compound which forms such salt being added per mol of naphthoquinone.

2. Process of claim 1 wherein the polar solvent is dimethylformamide.

3. Process of claim 1 wherein the polar solvent is dimethylacetamide.

4. Process of claim 1 wherein sodium acetate, potassium acetate or copper acetate is employed as the salt of acetic acid.

5. Process of claim 1 wherein sodium carbonate, potassium carbonate or sodium bicarbonate, is employed as the compound which forms an acetic acid salt under reaction conditions.

6. Process of claim 1 wherein potassium hydroxide or sodium hydroxide is employed as the compound which forms an acetic acid salt under the reaction conditions.

7. Process of claim 1 wherein the initial reaction is carried out in the presence of from 0.1 to 2 moles of acetic acid per mole of 1,4-naphthoquinone.

8. Process of claim 1 wherein the initial reaction is effected at a temperature of from 40° to 50° C.

9. Process of claim 1 wherein the initial reaction is carried out in the absence of oxygen.

10. Process of claim 1 wherein at least one mole of trans-1-acetoxybutadine is used per mole of 1,4-naphthoquinone.

* * * * *